US012491369B2

(12) United States Patent
Doerr et al.

(10) Patent No.: US 12,491,369 B2
(45) Date of Patent: Dec. 9, 2025

(54) IMPLANTABLE MEDICAL DEVICE WITH ELECTRODE DISLOCATION RECOGNITION

(71) Applicant: BIOTRONIK SE & Co. KG, Berlin (DE)

(72) Inventors: Thomas Doerr, Berlin (DE); Frank Becker, Berlin (DE); Christian Rehdorf, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 286 days.

(21) Appl. No.: 18/001,919

(22) PCT Filed: Jun. 1, 2021

(86) PCT No.: PCT/EP2021/064639
§ 371 (c)(1),
(2) Date: Dec. 15, 2022

(87) PCT Pub. No.: WO2021/259600
PCT Pub. Date: Dec. 30, 2021

(65) Prior Publication Data

US 2023/0233866 A1 Jul. 27, 2023

(30) Foreign Application Priority Data

Jun. 23, 2020 (EP) .................................... 20181572

(51) Int. Cl.
*A61N 1/00* (2006.01)
*A61N 1/362* (2006.01)
*A61N 1/37* (2006.01)

(52) U.S. Cl.
CPC ......... *A61N 1/3712* (2013.01); *A61N 1/3624* (2013.01); *A61N 1/3714* (2013.01)

(58) Field of Classification Search
None
See application file for complete search history.

(56) References Cited

U.S. PATENT DOCUMENTS 5,713,932 A * 2/1998 Gillberg ............... A61N 1/3622 607/9
2005/0096708 A1* 5/2005 Seim ........................ A61N 1/37 607/28

(Continued)

FOREIGN PATENT DOCUMENTS

EP 1234597 A2 8/2002
WO 0066219 A1 11/2000

OTHER PUBLICATIONS

International Search Report (PCT/ISA/210) and Written Opinion (PCT/ISA/237) mailed on Jun. 23, 2021, by the European Patent Office as the International Searching Authority for International Application No. PCT/EP2021/064639.

*Primary Examiner* — Niketa Patel
*Assistant Examiner* — Anant A Gupta
(74) *Attorney, Agent, or Firm* — Buchanan Ingersoll & Rooney PC

(57) ABSTRACT

An implantable medical device for stimulating a heart, includes a stimulation electrode configured to stimulate a first cardiac region of the heart, and a detection unit configured to detect an intracardiac electrogram at a second cardiac region (ventricle) of the heart. In operation, the device: delivers a stimulation pulse to the heart; evaluates a time and at least one morphologic parameter of a responsive signal of an intracardiac electrogram, wherein the at least one morphologic parameter is chosen from: an absolute value of the signal amplitude, a width of the signal, a positive, negative and/or total area under at least a part of the signal, and a number of occurrences and/or time of occurrence of zero crossings of the signal; and identifies a dislocation of the stimulation electrode if the time of the signal is below a first threshold value and the morphologic parameter exceeds a further threshold value.

12 Claims, 3 Drawing Sheets

(56) References Cited

U.S. PATENT DOCUMENTS

| | | | | |
|---|---|---|---|---|
| 2008/0255628 | A1* | 10/2008 | Seim | A61N 1/368 607/17 |
| 2010/0114221 | A1* | 5/2010 | Krause | A61N 1/36514 607/27 |
| 2012/0239106 | A1 | 9/2012 | Maskara et al. | |
| 2018/0161572 | A1* | 6/2018 | Gunderson | A61N 1/3706 |

* cited by examiner

IMPLANTABLE MEDICAL DEVICE WITH ELECTRODE DISLOCATION RECOGNITION

CROSS-REFERENCE TO RELATED APPLICATIONS

This application is the United States National Phase under 35 U.S.C. § 371 of PCT International Patent Application No. PCT/EP2021/064639, filed on Jun. 1, 2021, which claims the benefit of European Patent Application No. 20181572.7, filed on Jun. 23, 2020, the disclosures of which are hereby incorporated by reference herein in their entireties.

TECHNICAL FIELD

The present invention relates to an implantable medical device for stimulating a human or animal heart, to a method for determining a dislocation of the stimulation electrode of such an implantable medical device, and to a computer program product.

BACKGROUND

Implantable medical devices for stimulating a human or animal heart, such as pacemakers, have been known for a long time. They can perform different functions. Different stimulation programs can be carried out by an appropriate pacemaker to restore the treated heart to a normal state.

For properly carrying out all functions of such an implantable medical device, it is mandatory that its stimulation electrode is correctly positioned. However, electrode dislocation often occurs during the lifetime of such an implantable medical device.

U.S. Pat. No. 5,713,932 discloses a method and an apparatus for determining atrial lead dislocation. For this purpose, a test pace pulse is applied to the atrial pace/sense electrode. Afterwards, the immediately following ventricular depolarization is detected by a ventricular sense electrode. The interval between the delivered atrial pace pulse and the detected ventricular depolarization is compared with a threshold interval value. If the measured interval is longer than the threshold interval, it is assumed that the atrial pace/sense electrode is in contact with the right atrium and thus correctly positioned.

International Publication No. WO 00/66219 A1 discloses a method and an apparatus for determining the occurrence of a dislocation of an atrial electrode in a cardiac stimulation device. The apparatus comprises control means for employing an atrial pulse generator to provide atrial pacing pulses to the atrial electrode at a first energy level and subsequently employing the atrial pulse generator to provide higher energy atrial pacing pulses to the atrial electrode at a second, greater energy level. Once again, the intervals between pacing pulse and a response pulse are determined. Their duration is used for determining whether the atrial electrode is properly located.

Thus, the known methods for identifying a dislocation of an electrode rely on an evaluation of a time duration between a pacing pulse and the respective ventricular response signal. However, relying only on a time information can lead to a false positive identification of ventricular signals since noise and irregular cardiac signals might also be identified as regular and proper ventricular response to an atrial stimulation. This, in turn, might lead to the incorrect identification of an atrial electrode as being properly located, wherein the electrode is in fact dislocated.

The present disclosure is directed toward overcoming one or more of the above-mentioned problems, though not necessarily limited to embodiments that do.

SUMMARY

It is an object of the present invention to provide an implantable medical device for stimulating a human or animal heart and a corresponding method by which an electrode dislocation can be more accurately determined than according to devices and methods known from prior art.

At least this object is achieved with an implantable medical device for stimulating a human or animal heart having the features of claim 1. Such a device comprises a processor, a memory unit, a stimulation unit, and a detection unit. The stimulation unit comprises a stimulation electrode and is configured to stimulate a first cardiac region of a human or animal heart. The detection unit is configured to detect an intracardiac electrogram (IEGM) at a second cardiac region. The second cardiac region is distinct from the first cardiac region. To be more precise, the second cardiac region is a ventricle of the human or animal heart that is to be stimulated.

According to the present invention, the memory unit comprises a computer-readable program that causes the processor to perform the steps explained in the following when executed on the processor.

First, a stimulation pulse (pacing pulse) is delivered to a human or animal heart by the stimulation unit. If the stimulation electrode of the stimulation unit is correctly positioned, the stimulation pulse is delivered to the first cardiac region. If the stimulation electrode is improperly located (dislocated), the stimulation pulse might be delivered to another cardiac region, such as the second cardiac region.

Afterwards, a time and at least one morphologic parameter of the signal of an intracardiac electrogram is evaluated. This intracardiac electrogram is detected by the detection unit, i.e., it represents a ventricular activity of the stimulated heart. The signal has been generated in response to the stimulation pulse, i.e., the signal is in particular due to a ventricular depolarization immediately following the stimulation pulse. The at least one morphologic parameter is chosen from the group comprising of:

- an absolute value of an amplitude of the signal (9),
- a width of the signal (9),
- a positive and/or a negative and/or a total area under at least a part of the signal (9), and
- a number of occurrences and/or a time of occurrence of zero crossings of the signal (9).

To give an example, if the signal has an amplitude of −3 mV, the absolute value of the amplitude is 3 mV. Likewise, if the signal has an amplitude of +2.5 mV, the absolute value of the amplitude is 2.5 mV.

Finally, a dislocation of the stimulation electrode is identified if two conditions are met at the same time. According to the first condition, the time of the signal needs to be below a first threshold value. In this context, the term "time of the signal" means "time of the signal after delivery of the stimulation pulse". According to the second condition, the morphologic parameter needs to exceed at least one further threshold value. In this context, different threshold values are typically chosen for different morphologic parameters.

Expressed in other words, the presently claimed invention does not rely only on a time information of a ventricular signal detected in response to a stimulation pulse, but also considers at least one morphologic criterion of the detected signal in order to determine whether or not a dislocation of the stimulation electrode has been taken place. By also considering such a morphologic criterion (morphologic parameter), ventricular signals that can be attributed to noise or irregular cardiac signals can be safely separated from real ventricular signals so that a higher reliability of the dislocation identification as possible.

In an embodiment, the implantable medical device is a pacemaker such as an implantable pulse generator (IPG). In an embodiment, the implantable medical device is an implantable cardioverter/defibrillator (ICD). In an embodiment, the implantable medical device is specifically adapted to deliver an atrial antitachycardial therapy to the heart to be stimulated.

In an embodiment, a dislocation of the stimulation electrode is identified not only on the basis of a single evaluated signal, but rather on the basis of a plurality of ventricular signals caused by a previous stimulation pulse delivered by the stimulation unit. To give an example, 2, 3, 4, 5, 6, 7, 8, 9 or 10 ventricular signals can be evaluated as described above in order to identify a dislocation of the stimulation electrode. In an embodiment, 2 to 10, in particular 3 to 9, in particular 4 to 8, in particular 5 to 7 ventricular signals are evaluated is in order to identify a dislocation of the stimulation electrode.

In an embodiment, the stimulation electrode is considered to be dislocated if n-m evaluated ventricular signals fulfil the two criteria explained above. In this context, n is a number between 1 and 10, in particular between 2 and 9, in particular between 3 and 8, in particular between 4 and 7, in particular 5 or 6. Furthermore, m is a number between 0 and 9, in particular between 1 and 8, in particular between 2 and 7, in particular between 3 and 6, in particular 4 or 5. Furthermore, m is always smaller than n. To give an example, if 3 ventricular signals are evaluated (n=3) and 2 of these signals (m=1) fulfil the two conditions explained above, the stimulation electrode is considered to be dislocated.

In an embodiment, the computer-readable program causes the processor to evaluate two morphologic parameters of the ventricular signal, namely both the amplitude of the signal and the width of the signal. In doing so, the reliability of a correct identification of a ventricular signal can be increased.

In an embodiment, the computer-readable program causes the processor to identify dislocation of the stimulation electrode if the following two conditions are met. According to the first condition, the time of the signal is below a first threshold value (as already explained above). According to the second condition, the absolute value of the amplitude of the signal needs to traverse the further threshold value for the amplitude in two instances within a time exceeding the further threshold value for the width of the signal. The following example might be helpful in illustrating this embodiment: assuming a ventricular signal having a maximum amplitude of 4 mV is evaluated. Further assuming that the further threshold value for the amplitude is 2 mV, the absolute value of the amplitude of the signal traverses the maximum threshold once when the signal increases towards its maximum amplitude and once when the signal decreases again. Thus, it traverses the further threshold value for the amplitude in two instances. If the time distance between the two traversing events is longer than the further threshold value for the signal width, the two conditions are met. In such a case, the morphologic evaluation of the signal strongly indicates that the signal is a real signal and not caused by artefacts or noise. Rather, in case of noise or artefacts, the time distance between two instances of traversing the further threshold value for the amplitude would rather be significantly shorter than the further threshold value for the signal with. Thus, by combining a time information and morphologic criteria, a very accurate evaluation of the ventricular signal is possible.

In an embodiment, the first threshold value is at least 80 ms. In an embodiment, the first threshold value lies in a range between 80 ms and 200 ms, in particular between 50 ms and 90 ms, in particular between 120 ms and 160 ms. If the ventricular response signal is detected more closely to the stimulation pulse than after an expiration of the first threshold value, it is very likely that the stimulation pulse has not stimulated an atrial region of the heart, but rather directly a ventricular region (leading to a very quick ventricular response). Then, the stimulation electrode is considered to be dislocated since it directly stimulated a ventricular region of the heart (i.e., the second cardiac region), not a region distinct from the second cardiac region.

In an embodiment, the further threshold value for the amplitude is at least 2 mV. In an embodiment, the further threshold value for the amplitude lies in a range between 2 mV and 10 mV, in particular between 3 mV and 9 mV, in particular between 4 mV and 8 mV, in particular between 5 mV and 7 mV.

In an embodiment, the further threshold value for the width is at least 4 ms measured at an absolute value of the amplitude corresponding to the further threshold for the amplitude. In an embodiment, the further threshold for the width lies in a range between 4 ms and 40 ms, in particular between 6 ms and 18 ms, in particular between 8 ms and 16 ms, in particular between 10 ms and 14 ms, in particular between 10 ms and 35 ms, in particular between 15 ms and 30 ms.

In an embodiment, the at least one further threshold value is a relative value being determined in relation to a signal amplitude of the R wave of at least one cardiac cycle directly (immediately) or indirectly preceding the evaluated signal. Thus, the specific behavior of the heart to be stimulated can be taken into account in this embodiment in order to determine the at least one further threshold value for the morphologic parameter of the ventricular signal to be evaluated.

In an embodiment, the first cardiac region is an atrium or a His bundle of a human or animal heart. Thus, the stimulation electrode is, in this embodiment, configured and designed to either stimulate an atrium (in particular the right atrium) of the heart or the His bundle of the heart. By such stimulation, a ventricular response signal is to be expected if the atrioventricular stimulation pathway is still intact. If, however, a ventricular response signal can be detected much earlier than expected, this indicates that the stimulation electrode is no longer located within the atrium or at the His bundle, but rather has been dislocated into the ventricle of the heart that is to be stimulated. Then, this electrode can no longer be used for delivering stimulation pulses in the course of an atrial antitachycardial stimulation or in the course of other atrial stimulations or His bundle stimulations.

In an embodiment, the stimulation unit is configured and designed to apply an atrial antitachycardial stimulation to an atrium of a human or animal heart. Such an atrial antitachycardial stimulation can also be denoted as atrial antitachycardial pacing (atrial ATP). It is mandatory for such a stimulation that the stimulation electrode used is properly located within the atrium of the heart to be stimulated.

In an embodiment, the identification of the dislocation of the stimulation electrode can be carried out prior to, during, or after the delivery of a stimulation pulse or a stimulation therapy. An application prior to or during the (intended)

delivery of stimulation pulses or a stimulation therapy is particularly effective against undesired side effects of the stimulation pulses or the stimulation therapy.

In an embodiment, the computer-readable program causes the processor to prevent delivery of the stimulation pulses by the stimulation unit if a dislocation of the stimulation electrode has been identified. This safety procedure prevents delivery of stimulation pulses in case of an undesired dislocation of the stimulation electrode. In an embodiment, such interruption or blockage of a stimulation therapy can be communicated to a remote monitoring system so as to inform medical staff about the identified electrode dislocation. In such a case, it is possible to request the patient to visit a medical doctor in order to further examine and/or to correct the detected electrode dislocation.

In an embodiment, the computer-readable program causes the processor to perform the steps of delivering a stimulation pulse, of evaluating a time and at least one morphologic parameter of the signal of an intracardiac electrogram and of identifying a dislocation of the stimulation electrode in a time window of 5 seconds to 30 seconds, in particular of 10 seconds to 25 seconds, in particular of 15 seconds to 20 seconds prior to an intended stimulation of the first cardiac region. Thus, the test whether or not the stimulation electrode is dislocated is, in this embodiment, carried out immediately prior to the therapeutic stimulation of the heart. Then, a delivery of stimulation pulses can be prevented in case of a dislocation of the electrode. This might be helpful and medically required since a stimulation by a dislocated stimulation electrode can have severe negative effects outbalancing any positive effects achieved by such stimulation.

In an embodiment, the computer-readable program causes the processor to perform the step of delivering a stimulation pulse at the beginning of a time window in which no intrinsic ventricular signal is expected to occur. Then, any interferences with intrinsic ventricular signals are avoided. Such time window can be a time window lying in a range of 50 ms to 1 second, in particular of 60 ms to 900 ms, in particular of 70 ms to 800 ms, in particular of 80 ms to 700 ms, in particular of 90 ms to 600 ms, in particular of 100 ms to 500 ms, in particular of 150 ms to 400 ms, in particular of 200 ms to 350 ms, in particular of 250 ms to 300 ms.

In an aspect, the present invention relates to a method for determining a dislocation of a stimulation electrode of the stimulation unit. The stimulation unit forms part of an implantable medical device for stimulating a human or animal heart, in particular an implantable medical device according to the preceding explanations. Furthermore, the stimulation unit is configured to stimulate a first cardiac region of a human or animal heart. The method comprises the steps explained in the following.

First, a stimulation pulse is delivered to a human or animal heart by the stimulation unit. If the stimulation electrode of the stimulation unit is correctly positioned, the stimulation pulse is delivered to the first cardiac region. If the stimulation electrode is improperly located (dislocated), the stimulation pulse might be delivered to another cardiac region, such as the second cardiac region.

Afterwards, a time and at least one morphologic parameter of the signal of an intracardiac electrogram is evaluated. This intracardiac electrogram is detected by the detection unit, i.e., it represents a ventricular activity of the stimulated heart. The signal has been generated in response to the stimulation pulse, i.e., the signal is in particular due to a ventricular depolarization immediately following the stimulation pulse. The at least one morphologic parameter is chosen from the group comprising of:

- an absolute value of an amplitude of the signal (9),
- a width of the signal (9),
- a positive and/or a negative and/or a total area under at least a part of the signal (9), and
- a number of occurrences and/or a time of occurrence of zero crossings of the signal (9).

Finally, a dislocation of the stimulation electrode is identified if two conditions are met at the same time. According to the first condition, the time of the signal needs to be below a first threshold value. According to the second condition, the morphologic parameter needs to exceed at least one further threshold value. In this context, different threshold values are typically chosen for different morphologic parameters.

In an aspect, the present invention relates to computer program product (in particular to a non-transitory computer program product) comprising computer-readable code that causes the processor to perform the steps explained in the following when executed on the processor.

First, a stimulation pulse is delivered to a human or animal heart by a stimulation unit comprising a stimulation electrode. If the stimulation electrode is correctly positioned, the stimulation pulse is delivered to the first cardiac region. If the stimulation electrode is improperly located (dislocated), the stimulation pulse might be delivered to another cardiac region, such as the second cardiac region.

Afterwards, a time and at least one morphologic parameter of the signal of an intracardiac electrogram is evaluated. This intracardiac electrogram is detected by the detection unit, i.e., it represents a ventricular activity of the stimulated heart. The signal has been generated in response to the stimulation pulse, i.e., the signal is in particular due to a ventricular depolarization immediately following the stimulation pulse. The at least one morphologic parameter is chosen from the group comprising of:

- an absolute value of an amplitude of the signal (9),
- a width of the signal (9), a positive and/or a negative and/or a total area under at least a part of the signal (9), and
- a number of occurrences and/or a time of occurrence of zero crossings of the signal (9).

Finally, a dislocation of the stimulation electrode is identified if two conditions are met at the same time. According to the first condition, the time of the signal needs to be below a first threshold value. According to the second condition, the morphologic parameter needs to exceed at least one further threshold value. In this context, different threshold values are typically chosen for different morphologic parameters.

In a further aspect, the present invention relates to a method of treatment of a human or animal patient in need of such treatment by means of an implantable medical device for stimulating a human or animal heart, in particular an implantable medical device according to the preceding explanations. In this context, the implantable medical device comprises a processor, a memory unit, a stimulation unit and a detection unit. The stimulation unit comprises a stimulation electrode and is configured to stimulate a first cardiac region of a human or animal heart. The detection unit is configured to detect an intracardiac electrogram (IEGM) at a second cardiac region. The second cardiac region is distinct from the first cardiac region. To be more precise, the second cardiac region is a ventricle of the human or animal heart that is to be stimulated.

First, a stimulation pulse is delivered to a human or animal heart by the stimulation unit. If the stimulation electrode of the stimulation unit is correctly positioned, the stimulation pulse is delivered to the first cardiac region. If the stimulation electrode is improperly located (dislocated), the stimulation pulse might be delivered to another cardiac region, such as the second cardiac region.

Afterwards, a time and at least one morphologic parameter of the signal of an intracardiac electrogram is evaluated. This intracardiac electrogram is detected by the detection unit, i.e., it represents a ventricular activity of the stimulated heart. The signal has been generated in response to the stimulation pulse, i.e., the signal is in particular due to a ventricular depolarization immediately following the stimulation pulse. The at least one morphologic parameter is chosen from the group comprising of:

- an absolute value of an amplitude of the signal (9),
- a width of the signal (9),
- a positive and/or a negative and/or a total area under at least a part of the signal (9), and
- a number of occurrences and/or a time of occurrence of zero crossings of the signal (9).

Then, a dislocation of the stimulation electrode is identified if two conditions are met at the same time. According to the first condition, the time of the signal needs to be below a first threshold value. According to the second condition, the morphologic parameter needs to exceed at least one further threshold value. In this context, different threshold values are typically chosen for different morphologic parameters.

Finally, stimulation pulses are delivered to the human or animal heart by the stimulation unit if no dislocation of the stimulation electrode was identified in the preceding identifying step. In this context, the stimulation pulses serve for an atrial antitachycardial stimulation. If, on the other hand, a dislocation of the stimulation electrode has been identified in the preceding identifying step, delivering of stimulation pulses for atrial antitachycardial stimulation to the human or animal heart is prevented. Thus, a correct (proper) location of the stimulation electrode decides whether or not an atrial antitachycardial stimulation is carried out.

Expressed in other words, the determination of the correct positioning of the stimulation electrode is a mandatory prerequisite to be fulfilled in order to perform the intended atrial antitachycardial stimulation. Thus, the determination whether or not the stimulation electrode is properly located serves here as safety step in this medical method.

All embodiments of the implantable medical device can be combined in any desired way and can be transferred either individually or in any arbitrary combination to the described methods and the described computer program product. Likewise, all embodiments of the described methods can be combined in any desired way and can be transferred either individually or in any arbitrary combination to the respective other method, to the implantable medical device and to the computer program product. Finally, all embodiments described with respect to the computer program product can be combined in any desired way and can be transferred either individually or in any arbitrary combination to the described implantable medical device or to the described methods.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be described in the following making reference to exemplary embodiments and accompanying Figures. In the Figures.

DETAILED DESCRIPTION

Figure 1A:
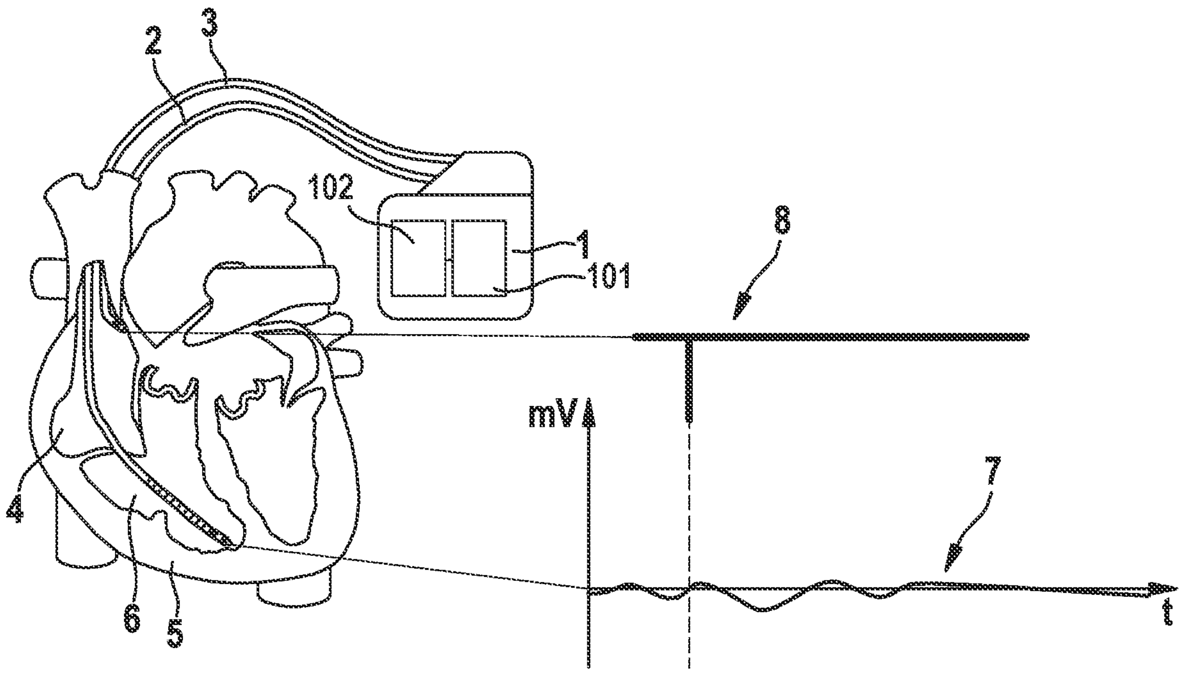
FIG. 1A shows a schematic depiction of a human heart with a correctly positioned atrial stimulation electrode.

FIG. 1A shows a cardiac pacemaker 1 serving as an implantable medical device for stimulating a human or animal heart. This cardiac pacemaker 1 comprises a processor 101, a memory unit 102 connected to the processor 101, a stimulation electrode 2 forming part of a stimulation unit, as well as a sensing electrode 3 forming part of a detection unit. The stimulation electrode 2 is located within an atrium 4 of a human heart 5 to be stimulated. The sensing electrode 3 is located in a ventricle 6 of the same heart 5.

The sensing electrode 3 serves for detecting an intracardiac electrogram 7 comprising ventricular signals such as ventricular depolarizations.

If a stimulation pulse 8 is delivered to the atrium 4 by the stimulation electrode 2, no significant ventricular signals can be observed in the intracardiac electrogram 7 within the depicted time interval. This is due to the fact that a ventricular depolarization responsive to the atrial stimulation pulse 8 only takes place after the atrioventricular response time (atrioventricular interval) has been passed. However, the intracardiac electrogram 7 only shows a time period shorter than the atrioventricular interval.

Figure 1B:
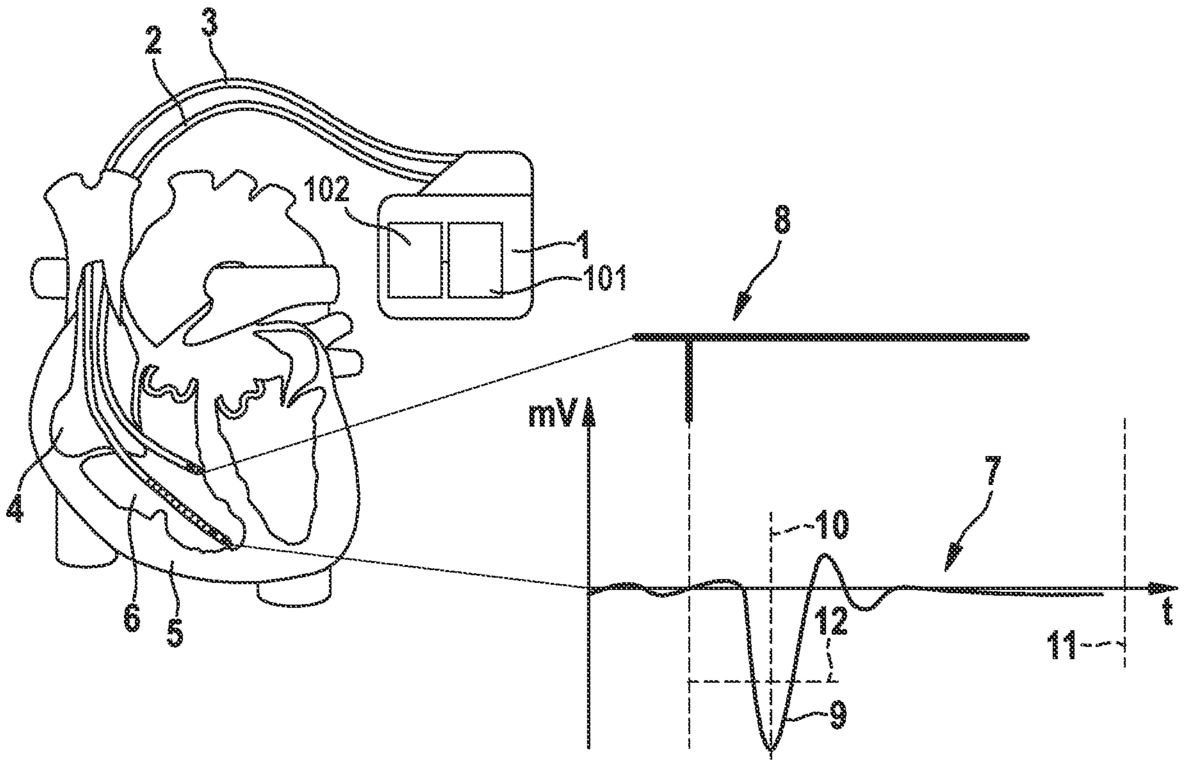
FIG. 1B shows a schematic depiction of human heart with a dislocated atrial stimulation electrode.

FIG. 1B shows a similar situation, wherein the same or similar elements are denoted in this and all following Figures with the same numeral references. In the situation displayed in FIG. 1B, the stimulation electrode 2 is dislocated so that it no longer contacts atrial tissue in the atrium 4 of the human heart 5 to be stimulated, but rather ventricular tissue in the ventricle 6 of the heart 5.

If now a stimulation pulse 8 is delivered by the stimulation electrode 2, an immediate ventricular response 9 can be observed in the intracardiac electrogram. This is due to the fact that the ventricular stimulation results in a very quick ventricular depolarization (much quicker than in case of atrioventricular stimulus conduction). The ventricular signal 9 occurs at a time 10 being lower than a threshold time 11 (serving as first threshold value). Although the voltage of the ventricular signal 9 is negative, its absolute value exceeds a set voltage threshold 12 (serving as further threshold value). Since the ventricular signal 9 occurs at a time point 10 being shorter than the set threshold 11 and has an amplitude, the absolute value of which exceeds the set amplitude threshold 12, the ventricular signal 9 is considered as real ventricular signal indicative for a dislocation of the stimulation electrode 2.

Figure 2:
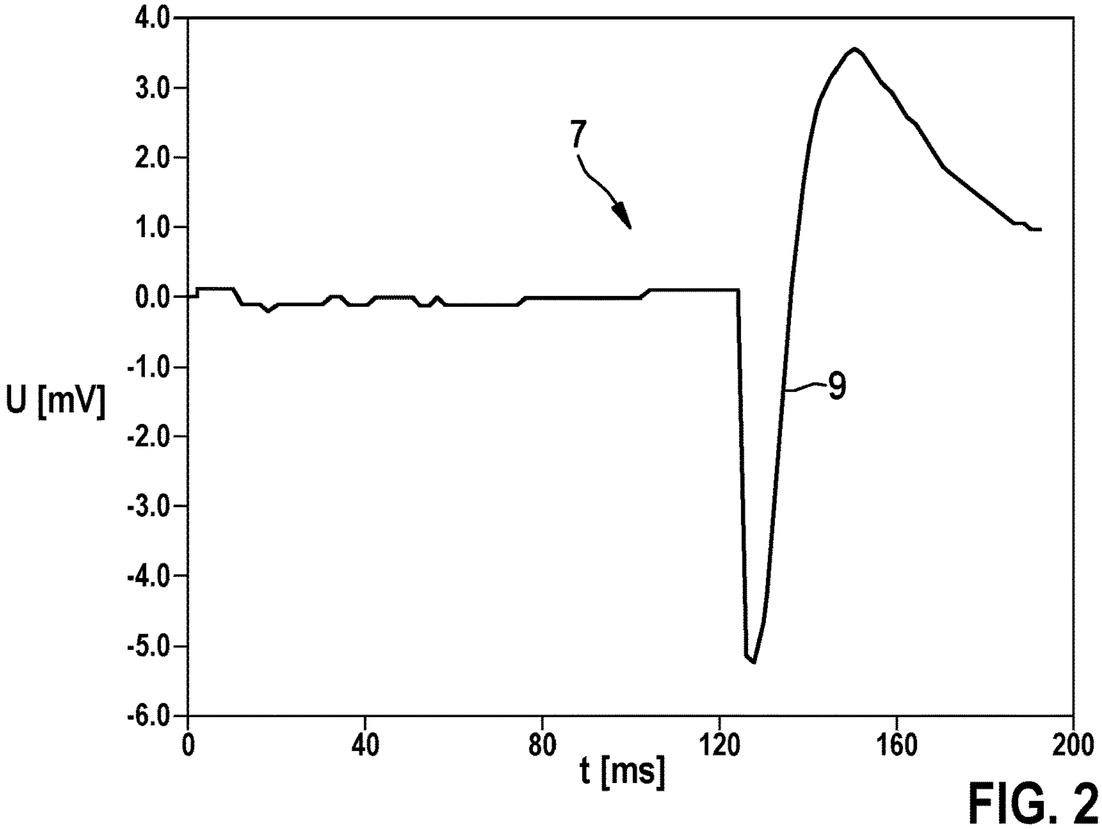
FIG. 2 shows a first exemplary intracardiac electrogram representative for a correctly located atrial stimulation electrode.

FIG. 2 shows a first exemplary intracardiac electrogram 7 comprising a morphologic signal response to an atrial stimulation (pacing) pulse. This intracardiac electrogram has been recorded with a ventricular electrode after an atrial pace/ventricular pace stimulation sequence. In this case, the atrial stimulation electrode is correctly fixed within the atrium, wherein the ventricular electrode is fixed within the apex of the right ventricle of the heart to be stimulated. After a stimulation by the atrial electrode, no immediate signal can be detected by the ventricular electrode within 120 ms after the atrial stimulation pulse. Only after a ventricular stimulation (approximately at 130 ms), a typical signal response 9 after ventricular capture can be observed.

Figure 3:
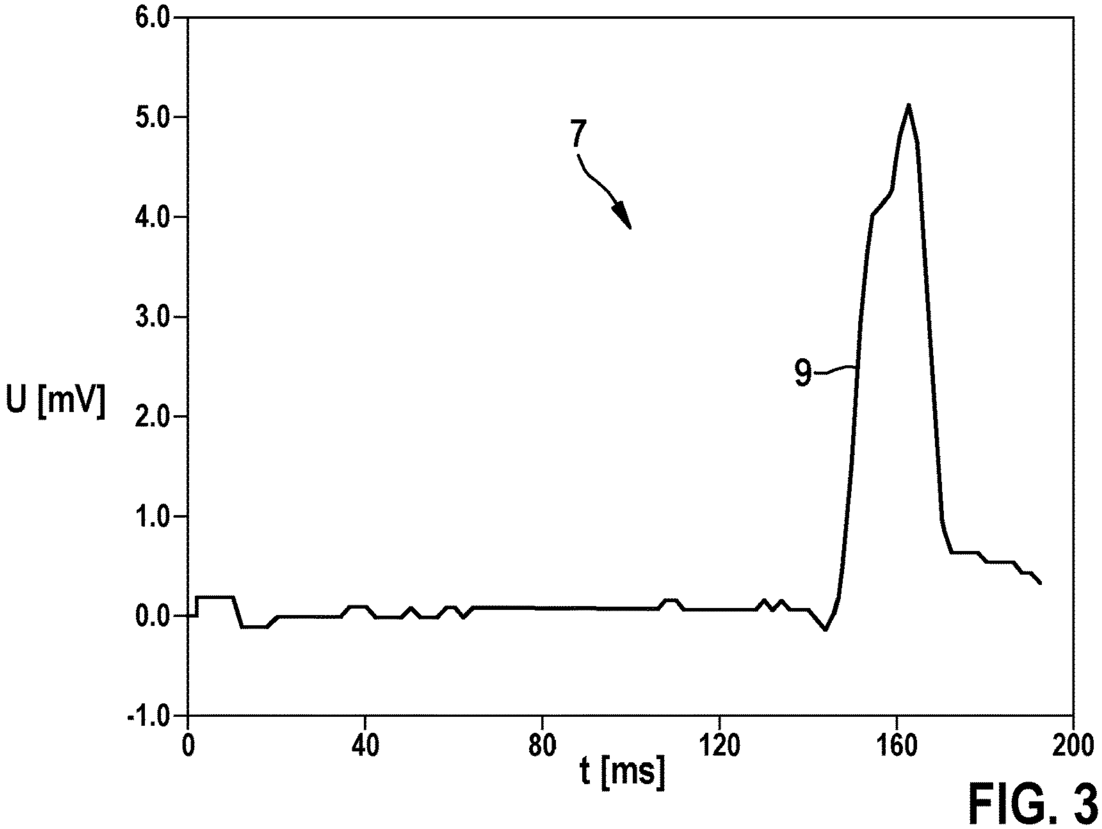
FIG. 3 shows a second exemplary intracardiac electrogram representative for a correctly located atrial stimulation electrode.

FIG. 3 shows a second exemplary electrocardiogram 7 comprising a morphologic signal response recorded at a ventricular electrode after an atrial pacing/ventricular sensing sequence. Also in this case, the atrial electrode is correctly positioned within the atrium. Likewise, the ventricular electrode is fixed within the apex of the right ventricle. In response to the stimulation with the atrial stimulation electrode, no immediate signal response can be observed within 140 ms after the atrial stimulation pulse. Only after an intrinsic transmission of the atrial stimulation into the ventricle, a typical signal response 9 for an intrinsic ventricular depolarization can be observed at approximately 160 ms.

Figure 4:
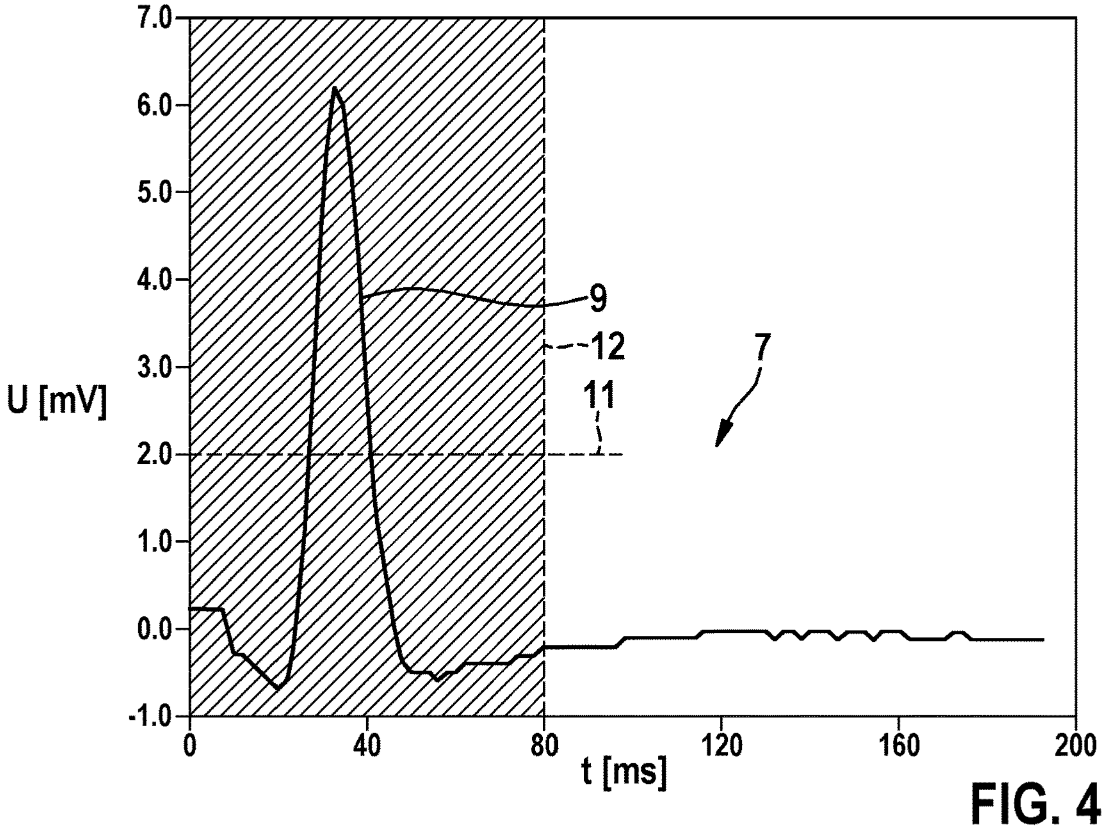
FIG. 4 shows a third exemplary intracardiac electrogram representative for a dislocated atrial stimulation electrode.

FIG. 4 shows a third exemplary intracardiac electrogram 7 comprising a morphologic signal response recorded at a ventricular electrode after pacing with an atrial electrode. In this case, the atrial electrode is not correctly positioned within the atrium of the heart to be stimulated, but has rather been dislocated into the ventricle of the heart. Here, it is located in a high-septal position. The stimulation with the stimulation electrode results in an immediate ventricular signal 9 at less than 40 ms. Such an early response is typically for an intrinsic ventricular stimulation that can, however, be allocated to the stimulation by the atrial electrode due to its early occurrence after the stimulation pulse with the atrial stimulation electrode. Since the ventricular signal 9 exceeds a set threshold for the amplitude 12 and occurs prior to a set threshold value 11 for the time, it is considered as indication that the atrial stimulation electrode has been dislocated.

Figure 5:
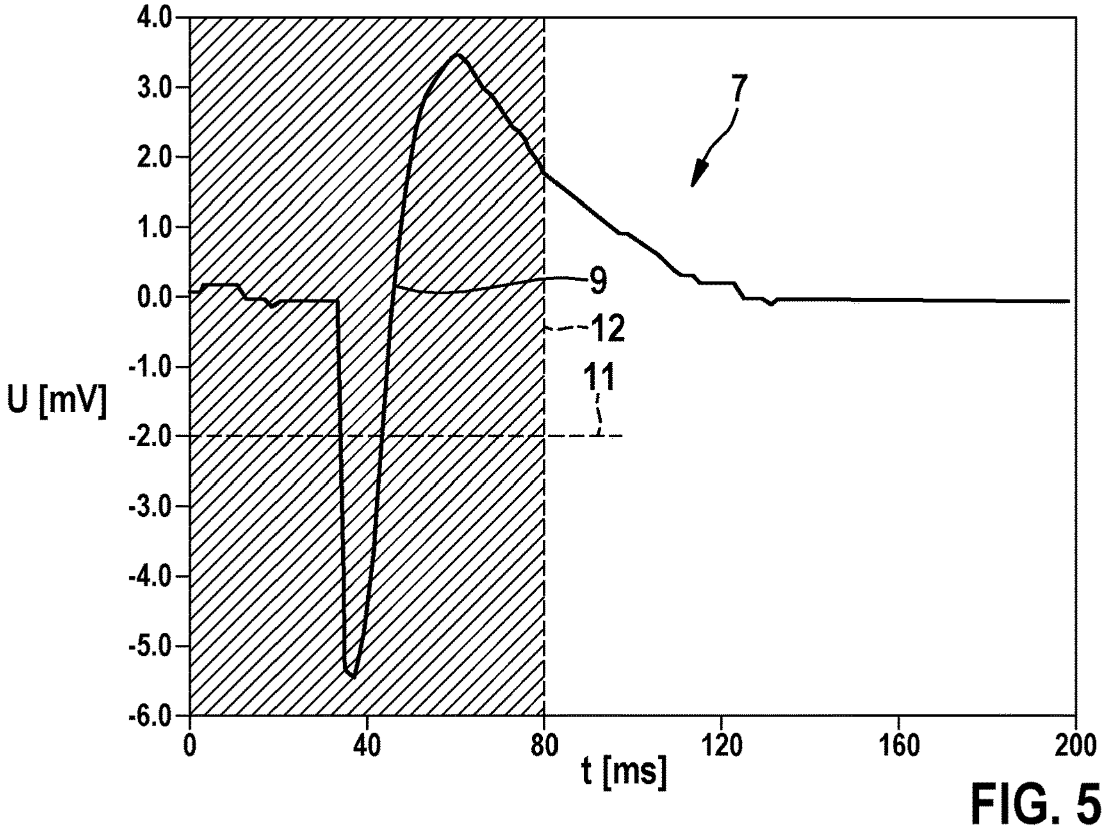
FIG. 5 shows a fourth exemplary intracardiac electrogram representative for a dislocated atrial stimulation electrode.

A similar situation is depicted in FIG. 5 showing another intracardiac electrogram 7 comprising a morphologic signal response recorded at a ventricular electrode after pacing with an atrial electrode. In this case, the atrial electrode has been dislocated into the ventricle and is now located at an apical position. After stimulation with the stimulation electrode, a signal response 9 can be detected at less than 20 ms that can be allocated as ventricular depolarization responsive to a ventricular stimulation pulse delivered by the atrial stimulation electrode. Since an absolute value of the ventricular signal 9 once again exceeds a threshold of 2 mV used as threshold value 12 for the amplitude and—at the same time—occurs earlier than a set threshold 11 for the time, also this ventricular signal 9 is considered as indicator for a dislocation of the atrial stimulation electrode.

Summarizing, ventricular signal responses to an atrial stimulation as shown in FIGS. 2 and 3 are indicative for a correctly positioned atrial stimulation electrode. In contrast, ventricular responses to a stimulation with a stimulation electrode as shown in FIGS. 4 and 5 are indicative for a dislocated atrial stimulation electrode. At least the amplitude and a temporal correlation with the stimulation pulse are used to distinguish between a correctly positioned stimulation electrode and a dislocated stimulation electrode. Further morphologic parameters like a signal which can also be used for making such decision.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. Implantable medical device for stimulating a human or animal heart, comprising a processor, a memory unit, a stimulation unit comprising a stimulation electrode configured to stimulate a first cardiac region of a human or animal heart, and a detection unit configured to detect an intracardiac electrogram at a second cardiac region of the same heart, the second cardiac region being a ventricle, wherein the memory unit comprises a computer-readable program that causes the processor to perform the following steps when executed on the processor:

deliver a stimulation pulse to a human or animal heart by the stimulation unit;

evaluate a signal of an intracardiac electrogram detected by the detection unit, the evaluation being based on a point in time in which the signal occurs and at least one morphologic parameter of the signal, the signal having been caused in response to the stimulation pulse, wherein the at least one morphologic parameter includes:

an absolute value of an amplitude of the signal, and at least one of:

a width of the signal, wherein the width of the signal is defined by a time interval between the time the amplitude of the signal exceeds a predefined threshold level and the time the amplitude of the signal falls below the predefined threshold level, a positive and/or a negative and/or a total area under at least a part of the signal, or a number of occurrences and/or an occurrence of zero crossings of the signal, identify a dislocation of the stimulation electrode if a) the point in time of the signal is below a first threshold value and b) the morphologic parameter exceeds at least one further threshold value; and prevent a delivery of further stimulation pulses by the stimulation unit when a dislocation of the stimulation electrode has been identified.

2. Implantable medical device according to claim 1, wherein the computer-readable program causes the processor to evaluate both the amplitude of the signal and the width of the signal.

3. Implantable medical device according to claim 1, wherein the first threshold value is at least 80 ms.

4. Implantable medical device according to claim 1, wherein the further threshold value for the amplitude is at least 2 mV.

5. Implantable medical device according to claim 1, wherein the at least one further threshold value is a relative value that is determined in relation to a signal amplitude of an R wave of at least one cardiac cycle preceding the evaluated signal.

6. Implantable medical device according to claim 1, wherein the first cardiac region is an atrium or a His bundle of a human or animal heart.

7. Implantable medical device according to claim 1, wherein the stimulation unit is configured and designed to apply an atrial antitachycardial stimulation to an atrium of a human or animal heart.

8. Implantable medical device according to claim 1, wherein the computer-readable program causes the processor to perform the steps of delivering a stimulation pulse, of evaluating a point in time in which a signal occurs and at least one morphologic parameter of the signal of an intracardiac electrogram and of identifying a dislocation of the stimulation electrode in a time window of 5 seconds to 30 seconds prior to an intended stimulation of the first cardiac region.

9. Implantable medical device according to claim 1, wherein the computer-readable program causes the processor to perform the step of delivering a stimulation pulse at the beginning of a time window in which no intrinsic ventricular signal is expected to occur.

10. Method for determining a dislocation of a stimulation electrode of a stimulation unit of an implantable medical device for stimulating a human or animal heart, the stimulation unit being configured to stimulate a first cardiac region of a human or animal heart, the method comprising the following steps:

delivering a stimulation pulse to a human or animal heart by a stimulation unit comprising a stimulation electrode;

evaluating a signal of an intracardiac electrogram detected by a detection unit, the evaluation being based on a point in time in which the signal occurs and at least one morphologic parameter of the signal, the detection unit configured to detect an intracardiac electrogram at a second cardiac region of the same heart, the second cardiac region being a ventricle, wherein the signal has been caused in response to the stimulation pulse, wherein the at least one morphologic parameter includes:

an absolute value of an amplitude of the signal, and at least one of:

a width of the signal, wherein the width of the signal is defined by a time interval between the time the amplitude of the signal exceeds a predefined threshold level and the time the amplitude of the signal falls below the predefined threshold level, a positive and/or a negative and/or a total area under at least a part of the signal, or a number of occurrences and/or an occurrence of zero crossings of the signal, identifying a dislocation of the stimulation electrode if a) the point in time of the signal is below a first threshold value and b) the morphologic parameter exceeds at least one further threshold value; and preventing a delivery of further stimulation pulses by the stimulation unit when a dislocation of the stimulation electrode has been identified.

11. Computer program product in a form of a non-transitory computer readable medium comprising computer-readable code that causes a processor to perform the following steps when executed on the processor:

delivering a stimulation pulse to a human or animal heart by a stimulation unit comprising a stimulation electrode;

evaluating a signal of an intracardiac electrogram detected by a detection unit, the evaluation being based on a point in time in which the signal occurs and at least one morphologic parameter of the signal, the detection unit configured to detect an intracardiac electrogram at a second cardiac region of the same heart, the second cardiac region being a ventricle, wherein the signal has been caused in response to the stimulation pulse, wherein the at least one morphologic parameter includes:

an absolute value of an amplitude of the signal, and at least one of:

a width of the signal, wherein the width of the signal is defined by a time interval between the time the amplitude of the signal exceeds a predefined threshold level and the time the amplitude of the signal falls below the predefined threshold level, a positive and/or a negative and/or a total area under at least a part of the signal, or a number of occurrences and/or a time of occurrence of zero crossings of the signal, identifying a dislocation of the stimulation electrode if a) the point in time of the signal is below a first threshold value and b) the morphologic parameter exceeds at least one further threshold value; and preventing a delivery of further stimulation pulses by the stimulation unit when a dislocation of the stimulation electrode has been identified.

12. Method of treatment of a human or animal patient in need of such treatment by means of an implantable medical device for stimulating a human or animal heart, wherein the implantable medical device comprises a processor, a memory unit, a stimulation unit comprising a stimulation electrode configured to stimulate a first cardiac region of a human or animal heart, the first cardiac region being an atrium of the heart, and a detection unit configured to detect an intracardiac electrogram at a second cardiac region of the same heart, the second cardiac region being a ventricle, the method comprising the following steps:

delivering a stimulation pulse to a human or animal heart by the stimulation unit;

evaluating a signal of an intracardiac electrogram detected by the detection unit, the evaluating based on a point in time in which the signal occurs and at least one morphologic parameter of the signal, wherein the signal has been caused in response to the stimulation pulse, wherein the at least one morphologic parameter includes:

an absolute value of an amplitude of the signal, and at least one of:

a width of the signal, wherein the width of the signal is defined by a time interval between the time the amplitude of the signal exceeds a predefined threshold level and the time the amplitude of the signal falls below the predefined threshold level, a positive and/or a negative and/or a total area under at least a part of the signal, or a number of occurrences and/or an occurrence of zero crossings of the signal, identifying a dislocation of the stimulation electrode if a) the point in time of the signal is below a first threshold value and b) the morphologic parameter exceeds at least one further threshold value;

delivering stimulation pulses for an atrial antitachycardial stimulation to the human or animal heart by the stimulation unit, if no dislocation of the stimulation electrode was identified in the preceding step, or preventing delivering stimulation pulses for an atrial antitachycardial stimulation to the human or animal heart by the stimulation unit, if a dislocation of the stimulation electrode was identified in the preceding step.

* * * * *